United States Patent [19]

Furugard et al.

[11] Patent Number: 4,821,327

[45] Date of Patent: Apr. 11, 1989

[54] ACOUSTICAL STETHOSCOPE WITH ELECTRICAL FILTER

[76] Inventors: Erik G. Furugard, 21 CH de la Source, CH-1296 Coppet, Switzerland; Charles Caron, Chable beaumont, Haute Savoie, France

[21] Appl. No.: 80,539
[22] PCT Filed: Oct. 8, 1986
[86] PCT No.: PCT/CH86/00140
  § 371 Date: Jun. 9, 1987
  § 102(e) Date: Jun. 9, 1987
[87] PCT Pub. No.: WO87/02233
  PCT Pub. Date: Apr. 23, 1987
[51] Int. Cl.$^4$ .............................................. A61B 7/04
[52] U.S. Cl. ..................................................... 381/67
[58] Field of Search .............................. 381/67, 72, 74

[56] References Cited
U.S. PATENT DOCUMENTS 3,247,324  4/1966  Cefaly et al. .
3,409,737  11/1968  Settler et al. .................... 381/67
3,651,798  3/1972  Egli et al. .
4,254,302  3/1981  Walshe ............................. 381/67
4,594,731  6/1986  Lewkowicz ..................... 381/67

FOREIGN PATENT DOCUMENTS 1084428  6/1960  Fed. Rep. of Germany .
2363317  3/1978  France .

*Primary Examiner*—Forester W. Isen
*Attorney, Agent, or Firm*—Gifford, Groh, Sheridan, Sprinkle and Dolgorukov

[57] ABSTRACT

The stethoscope comprises a membrane (2) sensor (1) connected by a tube (3) to ear-pieces (8 & 9). The tube (3) traverses a casing (10) containing an electrical unit connected by a cable (12) to an electrical sensor (11). The electrical unit is sensitive to a given frequency range and comprises an electro-acoustic emitter (19) supplying acoustic signals into conduit (3) which are obtained in response to signals coming from the sensor (11) according to a predetermined scheme.

6 Claims, 1 Drawing Sheet

ACOUSTICAL STETHOSCOPE WITH ELECTRICAL FILTER

SUMMARY OF THE INVENTION

Stethoscopes are largely used in medical applications, but they require a certain amount of skill. Thus, the measuring of the arterial pressure by auscultation can be made with precision. However, one has to take into account the impact of the operator, which is not negligible, on the results of the measurement, such as the auditive acuity, the environmental noise, reaction time etc.. The delicate point is, evidently, the determination of the diastolic pressure.

In certain devices designed for the purpose of a more or less automatic measurement of the arterial pressure, it is known to replace the regulate stethoscope by an electrical unit comprising a pick-up, at least one input filter, an amplifier and a threshold device for the purpose of supplying an electrical signal as soon as the level of the sounds perceived by the electrical pick-up, in a given frequency range, exceeds a predetermined threshold. There are also electrical stethoscopes based on the same principle, but which are not appreciated by the medical profession except for certain applications. In fact, doctors are used to the classical stethoscope and do not like to rely entirely on electrical stethoscopes. This compels them to use two different kinds of stethoscopes.

The aim of the present invention is to eliminate the waste of time resulting from the use of two different kinds of stethoscopes. The object of this invention is a stethoscope comprising an acoustical pick-up and an electrical pick-up, the latter being connected to an amplifier acting upon an electro-acoustical emitter transmitting sounds to the earpieces of the stethoscope, characterized in that the electrical receiver is connected to the emitter by way of a band pass filter, followed by a threshold device supplying a signal to drive the electro-acoustical emitter, the latter being connected to an audible frequency generator which supplies audible sounds as soon as the level of the sounds perceived by the electrical pick-up and included in the range of the passing frequencies of the filter exceeds a well-determined threshold.

The attached drawing represents schematically and by way of example an embodiment and some variants of the stethoscope which is the object of the invention.

DETAILED DESCRIPTION OF THE INVENTION

Figure 1:
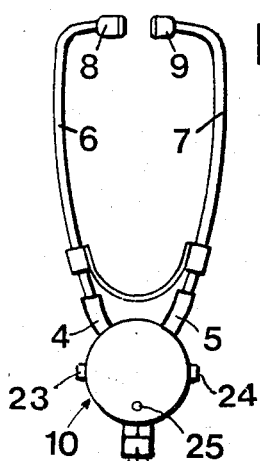
FIG. 1 is an exterior view of a stethoscope.

The stethoscope represented in FIG. 1, just like the regular stethoscopes, contains a capsule 1, covered by a flexible membrane 2 to form an acoustical pick-up. This capsule is connected to a flexible tube or conduit 3, which separates into two branches 4 and 5 ending in two bent tubes 6 and 7, whose upper ends are provided with butts 8 and 9 designed to fit into the auditive channels of the user.

This stethoscope further comprises an electrical unit enclosed in casing 10 which is connected to the acoustical conduit 3. This electrical unit is connected to a piezoelectrical pick-up 11 which is attached to membrane 2 by means of glue. The connection between the electrical unit in causing 10 and pick-up 11 is made by an armored or shielded cable 12 passing through conduit 3 and terminating in a contact plate 14 attached to the wall of capsule 1 and connected to the pick-up by two flexible conductors. Conduit 3 and armored cable 12 are connected to casing 10 by way of connector 13.

Figure 2:
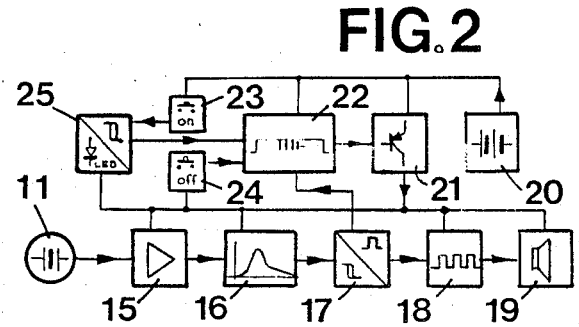
FIG. 2 is an synoptic electrical diagram of the electrical unit of this stethoscope.

FIG. 2 shows the diagram of the electrical unit which is connected to pick-up 11. The signal received from the pick-up is applied to an amplifier 15, then to bandpass filter 16 which strongly attenuates the frequencies below 20 Hz and above 100 Hz. The signals passing through filter 16 are those corresponding to the "Korotkoff noises" and enter into a Schmitt trigger 17 which controls generator 18 designed to apply hythmic sounds reproduced by emitter 19. The power supply to this unit is provided by battery 20 whose output is controlled by a transistor 21, The latter is controlled by an electrical timer 22 and this timer is controlled by a turn-on push-button 23 and a turn-off push-button 24 which renders transistor 21 conductive, respectively non-conductive, and which provides or does not provide power to circuits 15 to 19 and 24. Timer 22 is reactivated by circuit 17 every time that the latter circuit emits a pulse. The condition of battery 20 can be verified by the controlling device 25 which is activated during the closing period of push button 23.

Figure 3:
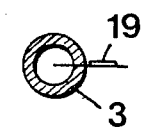
FIGS. 3 to 5 represent different methods of connecting the electro-acoustic emitter to the conduit of the stethoscope.

Emitter 19 can be connected in different ways to conduit 3 so that the signals supplied by it can be heard by the user. Thus, in FIG. 3, the electro-acoustic emitter 19 is composed of a vibrating plate, glued on, and passing through the wall of the acoustic conduit 3.

Figure 4:
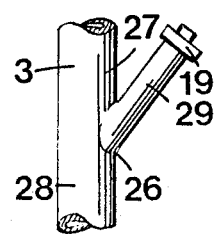

In the case of FIG. 4, conduit 3 shows a Y-shaped branching 26, one end 27 of which is connected to the acoustical pick up, one end 28 is connected to the earpieces, and a branch 29 is connected to the emitter 19. It is noted that branches 27 and 29 converge towards branch 28 which is connected to the ear-pieces in such a manner that the sounds emanating from emitter 19 are sent in a general direction corresponding to the normal direction of sound transmission of the acoustical sounds in conduit 3.

Figure 5:
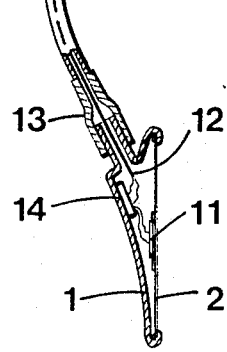

FIG. 5 shows a variant in which the acoustical emitter 19 is connected to a tube 30 passing through the wall of the acoustic conduit 3 and provided with a blend inside said conduit, so that its end 31 is directed towards the ear-pieces.

What is claimed is:

1. A stethoscope comprising an acoustic membrane pick-up for receiving sounds connected directly to acoustic earpieces by an acoustic conduit, an electrical pick-up mounted to respond to said sounds, an amplifier responsive to said electrical pick-up, an electro - acoustic emitter responsive to said amplifier for transmitting rhythmic sounds to said earpieces simultaneously with sounds from said acoustic membrane pick-up, further characterized in that said electro-acoustic emitter is connected to the electrical pick-up by way of a bandpass filter, followed by a threshold device, the threshold device being connected to an audible frequency generator which causes said acoustic emitter to emit said rhythmic sounds as soon as the level of sounds perceived by the electrical pick-up lying in the passband of the filter exceeds a well-determined threshold.

2. A stethoscope according to claim 1, characterized in that the electrical pick-up is attached to said acoustic membrane pick up.

3. A stethoscope according to claim 1, characterized in that the electro-acoustic emitter is set against the external surface of the acoustic conduit so that it transmits its signal through the wall of the acoustic conduit.

4. A stethoscope according to claim 1, characterized in that the acoustic conduit is provided with a branching, one branch of which is connected to the acoustic membrane pick-up, a second branch is connected to the earpieces and a third branch is connected to the electro-acoustic emitter.

5. A stethoscope according to claim 4, characterized in that the branching is in the shape of a Y, the lower branch of which is connected to the earpieces.

6. A stethoscope according to claim 1, characterized in that the electro-acoustic emitter is coupled to the acoustic conduit via a tube passing through the wall of the acoustic conduit, said tube being provided with a bend inside said conduit for the purpose of having the end of the tube directed towards the earpieces.

* * * * *

UNITED STATES PATENT AND TRADEMARK OFFICE
CERTIFICATE OF CORRECTION

PATENT NO. : 4,821,327

DATED : Apr. 11, 1989

INVENTOR(S) : Eric Furugard and Charles Caron

It is certified that error appears in the above-identified patent and that said Letters Patent is hereby corrected as shown below: On the title page:

In [76] Inventors: please delete "Erik G. Furugard" and insert -- Eric Furugard, Signed and Sealed this First Day of January, 1991

Attest:

HARRY F. MANBECK, JR.

*Attesting Officer*  *Commissioner of Patents and Trademarks*